(12) United States Patent
Fischer et al.

(10) Patent No.: US 9,932,284 B2
(45) Date of Patent: *Apr. 3, 2018

(54) PROCESS FOR THE SEPARATION OF 1,4-BUTANEDIOL AND CO-PRODUCTS

(71) Applicant: SHELL OIL COMPANY, Houston, TX (US)

(72) Inventors: Kai Jürgen Fischer, Amsterdam (NL); Wouter Koot, Amsterdam (NL); Sipke Hidde Wadman, Amsterdam (NL); Jean Paul Andre Marie Joseph Gishlain Lange, Amsterdam (NL)

(73) Assignee: SHELL OIL COMPANY, Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 14/892,436

(22) PCT Filed: May 28, 2014

(86) PCT No.: PCT/EP2014/061149
§ 371 (c)(1),
(2) Date: Nov. 19, 2015

(87) PCT Pub. No.: WO2014/191504
PCT Pub. Date: Dec. 4, 2014

(65) Prior Publication Data
US 2016/0107966 A1    Apr. 21, 2016

(30) Foreign Application Priority Data
May 31, 2013   (EP) .................................... 13169992

(51) Int. Cl.
*C07C 29/86* (2006.01)
*C07D 307/08* (2006.01)
*C07D 307/33* (2006.01)

(52) U.S. Cl.
CPC ............ *C07C 29/86* (2013.01); *C07D 307/08* (2013.01); *C07D 307/33* (2013.01)

(58) Field of Classification Search
CPC .................................................... C07C 29/86
See application file for complete search history.

(56) References Cited

U.S. PATENT DOCUMENTS

| | | | |
|---|---|---|---|
| 2,831,801 A | 4/1958 | Beckham et al. | |
| 4,032,583 A * | 6/1977 | Bowman et al. | C07C 29/80 568/868 |
| 4,032,683 A | 6/1977 | Coale | |
| 4,081,354 A | 3/1978 | Christman | |
| 4,447,643 A | 5/1984 | Feldman | |
| 4,966,658 A | 10/1990 | Berg | |
| 5,387,731 A | 2/1995 | Jenkins et al. | |
| 5,423,955 A | 6/1995 | Berg | |
| 6,023,003 A | 2/2000 | Dunning et al. | |
| 8,067,214 B2 | 11/2011 | Burk et al. | |
| 2005/0072663 A1 | 4/2005 | Laborie et al. | |
| 2009/0171129 A1 | 7/2009 | Evanko et al. | |
| 2011/0312050 A1 | 12/2011 | Zhang et al. | |
| 2012/0018293 A1 | 1/2012 | Kaasa et al. | |
| 2012/0184783 A1 | 7/2012 | Barnicki | |
| 2013/0284584 A1 | 10/2013 | Xiao et al. | |

FOREIGN PATENT DOCUMENTS

| | | |
|---|---|---|
| CN | 1216973 | 5/1999 |
| CN | 101959568 | 1/2011 |
| CN | 102295384 | 12/2011 |
| CN | 102643165 | 8/2012 |
| CN | 103396290 | 11/2013 |
| CN | 103664522 | 3/2014 |
| CN | 103772147 | 5/2014 |
| CN | 103772148 | 5/2014 |
| EP | 844228 | 5/1998 |
| JP | 2009256294 | 11/2009 |
| WO | 1995019946 | 7/1995 |
| WO | 2002022593 | 3/2002 |
| WO | 2010080038 | 7/2010 |
| WO | 2011028131 | 3/2011 |
| WO | 2012041990 | 4/2012 |
| WO | 2012130316 | 10/2012 |
| WO | 2013011462 | 1/2013 |

OTHER PUBLICATIONS

"Extraction THeory and General Procedure." Adapted from Mohrig. (c) Apr. 1, 2013. Available from: <https://web.archive.org/web/20130401055038/http://academics.wellesley.edu/Chemistry/chem211lab/Orgo_Lab_Manual/Appendix/Techniques/Extraction/extraction_n.html >.*
Ghanadzadeh, et al.: Experimental and Theoretical Study of the Phase Equilibria in Ternary Aqueous Mixtures of 1,4-Butanediol with Alcohols at 298.2 K j Chem Eng., 2009, 54, pp. 1009-1014.
Guan, Weihong: Heilongjiang Petrochemical Technology, vol. 11, No. 4, Dec. 31, 2000 The preparation and application of 1,4-butanediol, pp. 9-11, 1-16, 18-19.
Lange, Jean-Paul, et al.; Furfural—A Promisign Platform for Lignocellulosic Biofuels, ChemSusChem 2012, pp. 150-166.
Zeitsch, Karl. J.: The chemistry and technology of furfural and its many by-products. Elsevier, 2000.

(Continued)

*Primary Examiner* — Noble E Jarrell
*Assistant Examiner* — John S Kenyon

(57) ABSTRACT

The present invention provides a process for the recovery of 1,4-butanediol and at least one co-product selected from γ-butyrolactone, n-butanol and tetrahydrofuran from an aqueous stream, said process comprising the steps of providing the aqueous stream, providing a first solvent stream, combining said aqueous stream with said first solvent stream and recovering at least a portion of the 1,4-butanediol and at least a portion of at least one of the co-products by liquid-liquid extraction.

11 Claims, 3 Drawing Sheets

(56) References Cited

OTHER PUBLICATIONS

Hoydonckx, H.E., et al.: Furfural and Derivatives, in Ulmann's Encyclopedia or Industrial Chemistry, vol. 16, pp. 285-313, 2012.
Lange, J-P., et al.: Furfural—A Promising Platform for Lignocellulosic Biofuels; ChemSusChem, 5, pp. 150-166, 2012, Wiley-VCH Verlag GmBH & Co. KGaA, Weinheim.
Watson, James M.: Butane-1,4-diol from Hydrolytic Reduction of Furan, Ind. Eng. Chem. Prod. Res. Develop., vol. 12, No. 4, pp. 310-311, 1973.

\* cited by examiner

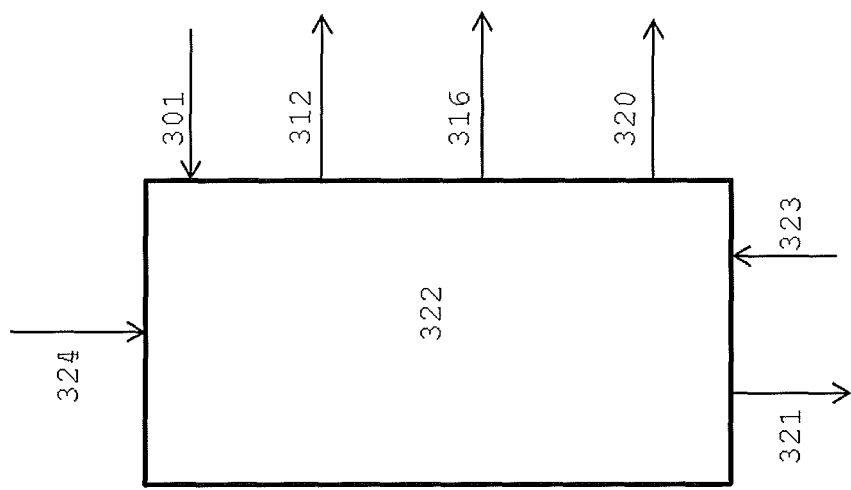

PROCESS FOR THE SEPARATION OF 1,4-BUTANEDIOL AND CO-PRODUCTS

PRIORITY CLAIM

The present application is a National Stage (§ 371) application of PCT/EP2014/061149, filed May 28, 2014, which claims priority from European Application 13169992.8 filed May 31, 2013, each of which are hereby incorporated by reference in their entirety.

FIELD OF THE INVENTION

The present invention relates to a process for the separation of 1,4-butanediol and co-products

BACKGROUND OF THE INVENTION 1,4-butanediol (1,4-BDO) and is a valuable chemical used industrially as a solvent and in the production of elastic fibres such as elastane/spandex, polybutyrate terephthalate and derivatives of gamma butyrolactone.

1,4-butanediol is produced industrially via a number of routes from petrochemical feedstocks, obtainable from fossil fuels. One industrial route requires the reaction of acetylene with two equivalents of formaldehyde followed by hydrogenation of the resultant 1,4-butynediol to form 1,4-butanediol. In an alternative process, propylene oxide is converted to allyl alcohol. The allyl alcohol is then hydroformylated to form 4-hydroxybutyraldehyde, which may be hydrogenated to form 1,4-butanediol. Another industrial process requires maleic anhydride as a starting material and proceeds via conversion to the methyl maleate ester and subsequent hydrogenation. Other traditional routes use butadiene, allyl acetate or succinic acid as starting materials.

1,4-butanediol may also be produced as a side-product in a method for making tetrahydrofuran (THF) by oxidizing n-butane to crude maleic anhydride followed by catalytic hydrogenation.

It is often the case that other desirable co-products, such as THF, γ-butyrolactone (GBL) and n-butanol are formed in processes that produce 1,4-butanediol. Such processes can be tailored to make more or less of each of these chemicals.

In recent years, increased efforts have focused on producing chemicals, including 1,4-BDO and the desirable co-products, from renewable feedstocks, such as sugar-based materials. U.S. Pat. No. 8,067,214 describes a biosynthetic pathway to produce 1,4-BDO directly from sugar using a non-naturally occurring microbial organism.

A further method for obtaining 1,4-butanediol and one or more of the desirable co-products (particularly THF) from non-fossil fuel based sources involves the decarboxylation of furfural and proceeds via an intermediate such as furan. Examples of reaction processes for achieving these steps can be found in Hoydonck, H. E., Van Rhijn, W. M., Van Rhijn, W., De Vos, D. E. & Jacobs, P. A. (2012) Furfural and Derivatives, in Ulmann's Encyclopedia or Industrial Chemistry (volume 16, pp 285-313), Wiley-VCH Verlag GmBH & Co. KGaA, Weinheim; Dunlop, A. P. and Peters, F. N., in The Furans Reinhold Publ. Co, 1953; K. J. Zeitsch, in "The Chemistry and Technology of Furfural and its Many By-products" Sugar Series 13, Elsevier, 2000; Lange, J-P, van der Heide, E, van Buijtenen, J., and Price, R.; Furfural—A Promising Platform for Lignocellulosic Biofuels; Chem-SusChem 2012, 5, 150-166 and Watson, J. M., Ind. Eng. Chem. Prod. Res. Develop., 1973, 12(4), 310. Furfural may be obtained from hemicellulose via acid hydrolysis in the liquid phase as well as in the gas phase as described in WO 2002/22593 and WO 2012/041990.

Succinic acid is also available from bio-based resources, as described in Green Chem., 2009, 11, 13, and can be used as a starting material in the production of 1,4-butanediol as well as the other desirable co-products, such as γ-butyrolactone, n-butanol and tetrahydrofuran.

Many processes provide 1,4-BDO and co-products as products within an aqueous stream. Typically, the 1,4-BDO and whichever co-products are present are purified using an energy-intensive distillation process, which may be complicated by the presence of azeotropes.

It would, therefore, be advantageous to provide an improved method suitable for the recovery of at least 1,4-butanediol and its desirable co-products from aqueous streams.

SUMMARY OF THE INVENTION

Accordingly, the present invention provides a process for the recovery of 1,4-butanediol and at least one co-product selected from γ-butyrolactone, n-butanol and tetrahydrofuran from an aqueous stream, said process comprising the steps of providing the aqueous stream, providing a first solvent stream, combining said aqueous stream with said first solvent stream and recovering at least a portion of the 1,4-butanediol and at least a portion of at least one of the co-products by liquid-liquid extraction.

BRIEF DESCRIPTION OF THE DRAWINGS

FIGS. 1, 2 and 3 are schematic diagrams of exemplary, but non-limiting, embodiments of a process for the separation of 1,4-butanediol and THF as described herein.

DETAILED DESCRIPTION OF THE INVENTION

Figure 1:
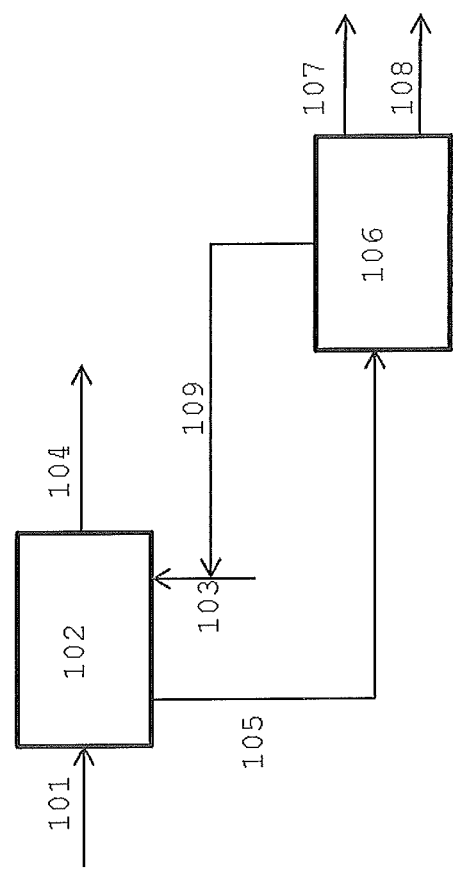

The present inventors have surprisingly found that 1,4-butanediol and its desirable co-products may be recovered together from an aqueous stream by the use of a solvent in liquid-liquid extraction. The separation of the solvent, 1,4-butanediol and the co-products present may then be achieved in a more facile manner than the usual separation of 1,4-butanediol, its co-products and water by a complicated multi-stage distillation process.

The term 'co-products' as used herein refers to γ-butyrolactone, n-butanol and tetrahydrofuran. Other materials, such as side-products and starting materials may also be present in the aqueous stream.

The present invention provides a process for the recovery of 1,4-butanediol and one or more of its co-products from an aqueous stream. The aqueous stream suitably comprises at least 0.1 wt %, preferably at least 5 wt %, more preferably at least 10 wt %, even more preferably at least 20 wt %, most preferably at least 25 wt % water based on the overall weight of the stream. The aqueous stream suitably comprises at most 99.9 wt %, preferably at most 95 wt %, more preferably at most 90 wt %, most preferably at most 75 wt % water based on the overall weight of the stream.

Preferably, the aqueous stream is the reaction product stream from a process for the production of 1,4-butanediol and/or THF in which 1,4-butanediol and at least one of its co-products are present. Particularly preferred reaction product streams include those produced in the processes involving the conversion of maleic anhydride to 1,4-butanediol and/or THF, the conversion of succinic acid to 1,4-butanediol and/or THF and the conversion of furan to 1,4-butanediol and/or THF. In each case, 1,4-butanediol and one or more of its co-products will be present in the reaction product stream. It is possible that 1,4-butanediol or any of the co-products may be the intended major product in the reaction product stream. More preferably, the aqueous stream is the reaction product stream from a process for the production of 1,4-butanediol and/or THF from bio-based, i.e. non fossil fuel base, feedstocks.

The 1,4-butanediol is typically present in the aqueous stream in an amount of at least 0.1 wt %, preferably at least 5 wt %, more preferably at least 10 wt %, even more preferably at least 25 wt %, typically at most 95 wt %, preferably at most 90 wt %, more preferably at most 80 wt %, most preferably at most 75 wt %, based on the weight of the overall stream.

The THF, if present, is typically present in the aqueous stream in an amount of at least 0.1 wt %, preferably at least 5 wt %, more preferably at least 10 wt %, even more preferably at least 25 wt %, typically at most 95 wt %, preferably at most 90 wt %, more preferably at most 80 wt %, most preferably at most 75 wt %, based on the weight of the overall stream.

The n-butanol, if present, is typically present in the aqueous stream in an amount of at least 0.1 wt %, preferably at least 5 wt %, more preferably at least 10 wt %, even more preferably at least 25 wt %, typically at most 95 wt %, preferably at most 90 wt %, more preferably at most 80 wt %, most preferably at most 75 wt %, based on the weight of the overall stream.

The GBL, if present, is typically present in the aqueous stream in an amount of at least 0.1 wt %, preferably at least 5 wt %, more preferably at least 10 wt %, even more preferably at least 25 wt %, typically at most 95 wt %, preferably at most 90 wt %, more preferably at most 80 wt %, most preferably at most 75 wt %, based on the weight of the overall stream.

As well as the 1,4-butanediol and its co-products, the aqueous stream may comprise other desirable and non-desirable materials. The nature and quantity of these other materials will depend on the process used to produce the 1,4-butanediol and the conditions used, including catalysts, reaction conditions such as temperature, pressure and saccharide concentration and starting materials. Depending on the process used to produce the 1,4-butanediol, the other materials present may include n-propanol as well as starting materials and other by-products.

The solvent in the first solvent stream suitably comprises a solvent that has a higher affinity for 1,4-butanediol and its co-products than water and shows a liquid-liquid phase split when mixed with water or saline water at appropriate process temperatures, preferably in the range of from 0 to 250° C. Suitable solvents are nitrogen- or oxygen-containing hydrocarbon-based solvents with these features. Preferable solvents are those with these features selected from the group of amines, alcohols, furanic compounds such as furfural, esters, ketones, aldehydes and combinations thereof, including compounds containing 2 or more of these functionalities.

In one embodiment of the invention, preferably, the solvent in the first solvent stream is an amine. In this embodiment, the solvent preferably comprises a primary, a secondary, a tertiary alkyl amine, or a combination thereof. Examples of suitable amines include paraffinic amines, naphthenic amines, aromatic amines, and mixtures thereof. More preferably, the amine is a tertiary amine. Even more preferably, the amine is a tertiary paraffinic amine.

Preferably, the amine contains carbon and nitrogen atoms in a ratio of at most 8:1 (carbon:nitrogen atoms).

Preferably, the amine contains an aliphatic cyclic group either containing the amine nitrogen or attached to the amine nitrogen.

Most preferably, the solvent is selected from the group consisting of N,N-dimethylcyclohexylamine (DMCA), methyl cyclohexyl amine, N-methyl piperidine, triethylamine, tripropylamine, or a combination thereof.

In another embodiment of the invention, preferably, the solvent in the first solvent stream is an alcohol, and more preferably it is selected from primary, secondary and tertiary $C_{4+}$ alcohols and mixtures thereof. Particularly suitable alcohols include n-butanol, n-pentanol and octanols, including 2-ethylhexanol.

The first solvent stream may be added to or combined with the aqueous stream in any amount sufficient to allow at least a portion of the 1,4-butanediol and at least a portion of one or more of its co-products, to dissolve in the solvent. Water may also dissolve in the solvent to the extent that the 1,4-butanediol and its co-products to water ratio in the extract stream is larger than in the aqueous stream. In certain embodiments, the amount of solvent in the first solvent stream added to or combined with the aqueous stream may be from 10 to 500 wt % of the total overall content of that stream.

Preferably, the ratio of solvent in the first solvent stream to 1,4-butanediol and its co-products may be the minimum amount for exceeding the solubility limit of the solvent in the aqueous stream to less than the amount needed to dissolve the entire aqueous stream. The amount of solvent in the first solvent stream added to or combined with the aqueous stream may suitably be at least 10 wt %, preferably at least 20 wt %, more preferably at least 25 wt % of the combined amount of 1,4-butanediol and its co-products in the aqueous stream. The amount of solvent in the first solvent stream added to or combined with the aqueous stream may suitably be at most 2000 wt %, preferably at most 500 wt %, more preferably at most 100 wt % of the combined amount of 1,4-butanediol and its co-products in the aqueous stream.

The aqueous stream is combined with the first solvent stream by any method suitable for the combination of two liquid streams, including but not limited to using a stirred mixer, passing the streams through a static mixer or by agitation. State of the art liquid-liquid contactors (extraction units) are, for example, a series of mixers and settlers, agitated extraction columns, packed extraction columns, SCHEIBEL® Columns, KARR® Columns, rotating disc contactor (RDC) columns, pulsed, packed (SMVP) and sieve tray columns. In a preferred embodiment of the invention, the two streams are combined in a counter-current extraction unit. In such a unit, the two streams are fed to the unit at points separated by at least 50% of the length, preferably substantially the entire length, of the unit and are brought into contact with each other while passing through the unit in a counter-current fashion.

The 1,4-butanediol and its co-products are recovered from the aqueous stream by liquid-liquid extraction after the first solvent stream has been added to or combined with said aqueous stream. For example, after the first solvent stream has been added to or combined with the aqueous stream, at least a portion of the 1,4-butanediol and at least a portion of the co-products present may be extracted into the solvent. The solvent, along with the 1,4-butanediol and the co-products may then be separated from the rest of the aqueous stream, forming a first 1,4-butanediol, co-products, and solvent rich stream (hereinafter termed the first desired material stream) and a first residual stream.

Preferably, any salt remains dissolved in the aqueous stream so that the separation process happens without precipitation of salts.

In certain embodiments, the liquid-liquid extraction may be enhanced by the inclusion of a synergist. Examples of suitable synergist include demulsifiers. Typical demulsifiers can be phenol-formaldehyde resins, epoxy resins, polyamines, di-epoxides or polyols.

Preferably, the method further comprises recovering the 1,4-butanediol, the co-products present, and/or solvent from the first desired material rich stream. The 1,4-butanediol, the co-products present, and/or solvent may be recovered from the first desired material stream through a distillation process. Said distillation may involve the separation of each material via any number of distillation steps with each material suitably forming either at least a part of the distillate or at least a part of the distillation bottoms depending on the other materials present in each step.

In one exemplary embodiment, the solvent may be removed from the other material in the first desired material rich stream and the 1,4-butanediol and the co-products present may then be separated from each other by a different method, e.g. distillation, extraction, etc.

In another exemplary embodiment, the first desired material rich stream may be distilled to form a first 1,4-butanediol rich stream, a first solvent rich stream and separate streams rich in each of the co-products present.

In each case, optionally, the solvent may be recycled.

Alternatively, the streams may be separated by an extractive process in which one or more of the materials are separated by extraction.

After carrying out the process of the invention, it is possible that there may be one or more of 1,4-butanediol and its co-products still present in the first residual stream. In one embodiment of the invention, it is preferable that further 1,4-butanediol and/or any of its co-products present are then recovered from the first residual stream by the steps of providing a second solvent stream, combining the first residual stream with said second solvent stream and recovering at least a portion of any remaining 1,4-butanediol and at least a portion of at least one of any remaining co-products present in the first residual stream by liquid-liquid extraction.

This process may be carried out under the same or different conditions to the recovery of 1,4-butanediol and its co-products from the original aqueous stream. Suitable conditions, equipment, quantities and materials may be selected from the conditions, equipment, quantities and materials detailed above as suitable for the recovery of 1,4-butanediol and its co-products from the original aqueous stream.

In this embodiment of the invention, combining the first residual stream with the second solvent stream may take place in the same or a different extraction unit as the combining of the aqueous stream and the first solvent stream.

In this embodiment of the invention, the 1,4-butanediol and/or any of its co-products present are recovered from the first residual stream by liquid-liquid extraction after the second solvent stream has been added to or combined with said first residual stream. For example, after the second solvent stream has been added to or combined with the first residual stream, a portion of the 1,4-butanediol and/or any of its co-products present may be extracted into the solvent. The solvent, along with the 1,4-butanediol and/or any of its co-products present may then be separated from the rest of the first residual stream, forming a second 1,4-butanediol and/or its co-products and solvent rich stream (hereinafter the second desired material rich stream) and a second residual stream.

Subsequent recovery of further 1,4-butanediol and/or its co-products may optionally be carried out in the same manner resulting in third and subsequent desired material rich streams and third and subsequent residual streams.

Preferably, in each case the method further comprises recovering the 1,4-butanediol, its co-products and/or solvent from the second, third and/or any subsequent desired material rich stream. The 1,4-butanediol and/or its co-products and/or solvent may be recovered from the second, third and/or any subsequent desired material rich stream through a distillation process as described above for the first desired material rich stream.

In a preferred embodiment of the invention, one or more of the first, second, third and subsequent residual streams may be recycled for use in the process in which the 1,4-butanediol is formed. Additional advantages of such a step include the reduction of the amount of waste produced and requiring disposal and also retaining any remaining 1,4-butanediol and/or desirable co-products in the system for subsequent recovery.

The process of the invention is preferably carried out at a temperature of at least 5° C., more preferably at least 10° C., even more preferably at least 20° C., even more preferably at least 25° C., most preferably at least 50° C. The temperature is preferably at most 250° C., more preferably at most 200° C., even more preferably at most 150° C. The pressure is preferably in the range of from 0.1 to 10 MPa, more preferably in the range of from 0.1 to 2.5 MPa, even more preferably in the range of from 0.1 to 1 MPa and must suitably be high enough to avoid vaporisation of the materials.

In a particularly preferred, but non-limiting, embodiment of the invention illustrated in FIG. 1, aqueous stream 101 is provided to a counter-current extraction unit 102 in which it is combined with first solvent stream 103. Liquid-liquid extraction provides a first residual stream 104 and a first desired material rich stream 105. The desired material rich stream 105 is then supplied to a distillation or other separation apparatus 106 to provide a 1,4-butanediol rich stream 107, a solvent rich stream 108, which is optionally recycled. Co-products, represented by stream 109 may be separated together or individually, i.e. stream 109 represents a GBL stream and/or a THF stream and/or an n-butanol stream.

In a further embodiment of the invention, the 1,4-butanediol and any of its co-products present may each be selectively removed from the aqueous stream by liquid-liquid extraction according to the process of the invention. In this embodiment, it will be necessary to use a solvent that has a different selectivity to each of 1,4-butanediol and its co-products present in the aqueous stream.

Figure 2:
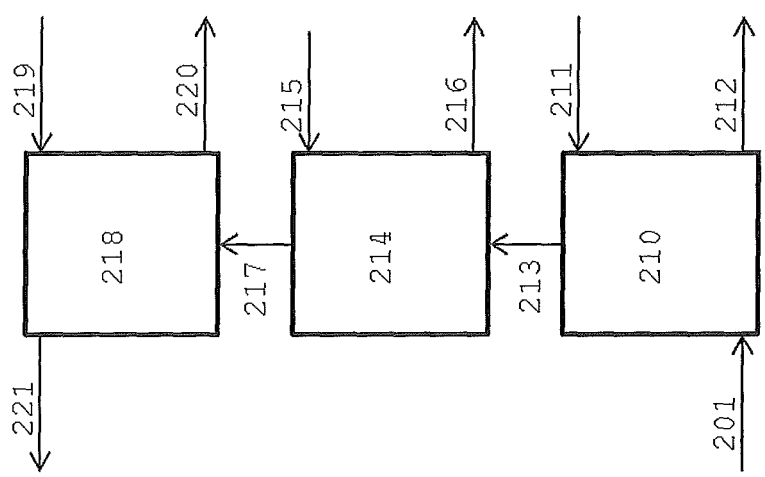

Selective extraction processes are demonstrated in the exemplary, but non-limiting embodiments shown in FIGS. 2 and 3.

In FIG. 2, the aqueous stream comprising 1,4-butanediol and its co-products is fed into a counter-current extraction unit comprising a number of extraction stages (three are shown here for illustrative purposes). The stream 201 is introduced to a first extraction stage 210, where it is contacted in a counter-current manner with a first solvent stream 211. A first solvent rich stream 212 containing one of the desired materials present (i.e. 1,4-butanediol or one of its co-products) is removed and the remaining aqueous stream 213 is then passed to a second extraction stage 214. In the second extraction stage 214, the remaining aqueous stream is contacted in a counter-current manner with a second stream 215 of the solvent. A second solvent rich stream 216 containing another of the desired materials present is removed and the remaining aqueous stream 217 is passed to a third extraction stage 218. In the third extraction stage 218, the remaining aqueous stream is contacted in a counter-current manner with a third stream 219 of the solvent. A third solvent rich stream 220 containing another of the desired materials present is removed and the remaining aqueous stream 221 is also removed for further purification, recycle or disposal.

If all of 1,4-butanediol, tetrahydrofuran, γ-butyrolactone and n-butanol are present in suitably high quantities, a fourth extraction stage may be used in order to extract the fourth desired material present.

In this embodiment, it will be readily understood that each extraction stage may contain one or more extraction processes. In this embodiment, which material is extracted at each point will depend on the solvent and any temperature profile present.

In a further exemplary, but non-limiting, embodiment illustrated in FIG. 3, the aqueous stream comprising 1,4-butanediol and its co-products 301 is fed into a counter-current extraction unit 322. Said extraction unit is also fed with first solvent stream 323, which is contacted with stream 301 in a counter-current manner. A first solvent rich stream 312, containing one of the desired materials present, is removed. Subsequently, a second solvent rich stream 316, containing another of the desired materials present, and a third solvent rich stream 320, containing a third desired material are removed. A residual stream 321 is also removed for further purification, recycle or disposal.

As with the embodiment shown in FIG. 2, if all of 1,4-butanediol, tetrahydrofuran, γ-butyrolactone and n-butanol are present in suitably high quantities, a fourth extraction step may be used to separate the fourth desired material present. In this embodiment, a fourth solvent rich stream, containing the fourth desired material will be removed.

Optionally, an additional aqueous stream 324 may be added to the extraction unit 322. The residual stream 321 may then be recycled and added to aqueous stream 324 before it is fed into extraction unit 322. In this case, the feed stream 301 may be located at any height (tray) in extraction unit 322, even below the first 312 or second 320 alcohol rich streams.

In this embodiment, as with that described in FIG. 2, which material is extracted at each point will depend on the solvent used and any temperature profile present.

EXAMPLES

Example 1

An aqueous stock solution was prepared containing 7.1 wt % tetrahydrofuran (THF) and 16.5 wt % 1,4-butanediol (BDO).

Example 2

5 gram of the stock solution described in Example 1 solution was contacted with 4 gram of dimethylcyclohex-ylamine. After separation of the layers, the organic and water phase were analyzed by GC. The organic phase contained 60% of the THF present and 40% of BDO present.

The invention claimed is:

1. A process for the recovery of 1, 4-butanediol and at least one co-product selected from γ-butyrolactone, n-butanol and tetrahydrofuran from an aqueous stream, said process comprising the steps of providing the aqueous stream, providing a first solvent stream, combining said aqueous stream with said first solvent stream and recovering at least a portion of the 1, 4-butanediol and at least a portion of at least one of the co-products by liquid-liquid extraction wherein at least one co-product is tetrahydrofuran.

2. The process according to claim 1, wherein the aqueous stream is derived from a reaction product stream from a process for the production of 1, 4-butanediol and/or THF.

3. The process according to claim 1, wherein at least a portion of the 1, 4-butanediol and at least a portion of at least one of the co-products present are recovered by liquid-liquid extraction by a process comprising the steps of extracting at least a portion of the 1, 4-butanediol and at least a portion of at least one of the co-products present into the solvent and separating a first 1, 4-butanediol, co-products and solvent rich stream, leaving a first residual stream wherein at least one co-product is tetrahydrofuran.

4. The process according to claim 3, wherein the 1, 4-butanediol, co-products and solvent rich stream is then separated into a 1, 4-butanediol rich stream, a solvent rich stream and separate streams each rich in one of the co-products present by distillation.

5. The process according to claim 1, wherein at least a portion of the 1, 4-butanediol and at least a portion of each of the co-products present are recovered by liquid-liquid extraction by a process comprising extracting at least a portion of the 1, 4-butanediol into a solvent stream to provide a first 1, 4-butanediol and solvent rich stream; extracting at least a portion of the THF, if present, into a solvent stream to provide a first THF and solvent rich stream; extracting at least a portion of the γ-butyrolactone, if present, into a solvent stream to provide a first γ-butyrolactone and solvent rich stream; and extracting at least a portion of the n-butanol, if present, into a solvent stream to provide a first n-butanol and solvent rich stream, leaving a residual stream.

6. The process according to claim 1, wherein the solvent is an amine.

7. The process according to claim 6, wherein the solvent is a tertiary amine.

8. The process according to claim 6, wherein the solvent is selected from the group consisting of dimethyl-cyclohexyl amine, methyl cyclohexyl amine, N-methyl piperidine, tri-ethylamine, tripropylamine, or a combination thereof.

9. The process according to claim 1, wherein the solvent is an alcohol.

10. The process according to claim 9, wherein the solvent is selected from n-butanol, n-pentanol and octanols.

11. The process according to claim 3, wherein any residual stream is recycled to the process in which the 1, 4-butanediol was formed.

* * * * *